United States Patent [19]

Listerud et al.

[11] Patent Number: 5,271,399
[45] Date of Patent: Dec. 21, 1993

[54] THREE DIMENSIONAL FOURIER TRANSFORM, FAST SPIN ECHO, BLACK BLOOD MAGNETIC RESONANCE ANGIOGRAPHY

[75] Inventors: John Listerud, Philadelphia, Pa.; Scott Atlas, Princeton, N.J.

[73] Assignee: Trustees of the University of Pennsylvania, Philadelphia, Pa.

[21] Appl. No.: 799,359

[22] Filed: Nov. 27, 1991

[51] Int. Cl.$^5$ .............................................. A61B 5/055
[52] U.S. Cl. .................................. 128/653.3; 324/306; 324/309
[58] Field of Search ............... 128/653.2, 653.3, 653.4; 324/306, 309

[56] References Cited

U.S. PATENT DOCUMENTS

| | | | |
|---|---|---|---|
| 3,138,259 | 8/1992 | Schmitt et al. | 324/309 |
| 4,918,386 | 4/1990 | Dumoulin et al. | 324/309 |
| 4,937,526 | 6/1990 | Ehman et al. | 324/309 |
| 4,968,935 | 11/1990 | Ehman et al. | 324/306 |
| 4,986,272 | 1/1991 | Riederer et al. | 324/309 |
| 5,043,665 | 8/1991 | Kuhara et al. | 324/309 |
| 5,070,876 | 12/1991 | Wright | 324/306 |
| 5,101,156 | 3/1992 | Pelc | 324/306 |
| 5,133,357 | 7/1992 | Dumoulin et al. | 128/653.3 |
| 5,151,656 | 9/1992 | Maier et al. | 324/309 |
| 5,168,226 | 12/1992 | Hinks | 324/309 |

FOREIGN PATENT DOCUMENTS 0471500 2/1992 European Pat. Off. ............ 324/309

OTHER PUBLICATIONS

R. R. Edelman, et al., Clinical Magnetic Resonance Imaging, W. B. Saunders (USA) (1990).
D. Twieg, "The K-Space Trajectory Formulation Of The NMR Imaging Process With Applications In Analysis And Synthesis Of Imaging Methods", Medical Physics, vol. 5, pp. 140–151 (1983).
J. Listerud, "First Principles Of Magnetic Resonance Angiography", Magnetic Resonance Quarterly, vol. 7, No. 2, pp. 136–170 (1991).
R. R. Edelman, et al., "Extracranial Carotid Arteries: Evaluation With Black Blood Angiography", Radiology vol. 177, pp. 45–50 (1990).

Primary Examiner—Lee S. Cohen
Assistant Examiner—K. M. Pfaffle
Attorney, Agent, or Firm—Woodcock Washburn Kurtz Mackiewicz & Norris

[57] ABSTRACT

Methods for producing an angiograph of a body portion are disclosed as including the steps of subjecting the body portion to electromagnetic energy so as to cause a response related to the magnetization of the body portion. Fast spin echo magnetic resonance measurements are performed on a three dimensional section of the body portion to generate three dimensional intensity information. The three dimensional intensity information is thereafter processed to construct an angiograph. In a preferred embodiment magnetic resonance data is produced by generating a slice gradient, generating a z axis slab selective 90° pulse, generating a z axis slab selective 180° pulse, generating a first phase encoding gradient pulse for a particular $K_y$ coordinate, generating a second phase encoding gradient pulse for a particular $K_z$ coordinate, and generating an x frequency encoding gradient and reading echo signal data from the body portion resulting from the 180° pulse. The method is repeated from the step of generating the 180° pulse, wherein the particular $K_z$ coordinate is incremented for each repetition. The method is thereafter repeated from the step of generating a 90° pulse, wherein the particular $K_y$ component is incremented after the $K_z$ coordinate has been incremented a prescribed number of times. Echo signal data read from the body portion is processed to produce an image.

10 Claims, 1 Drawing Sheet

THREE DIMENSIONAL FOURIER TRANSFORM, FAST SPIN ECHO, BLACK BLOOD MAGNETIC RESONANCE ANGIOGRAPHY

FIELD OF THE INVENTION

The present invention relates generally to the field of angiography and more particularly to the production of angiographs using magnetic resonance techniques.

BACKGROUND OF THE INVENTION

Measurement of blood flow, in vivo, is important for the functional assessment of the circulatory system. Angiography has become a standard technique for making such functional assessments. Typically, an arterial catheterization is performed on a subject, for whom an angiograph is to be prepared, wherein a so-called "contrast agent" or iodinated contrast agent is introduced, after which radiographic imaging is performed.

Radiographic imaging of the body is well known and extremely useful as a diagnostic tool in the medical arts. Radiographic imaging involves positioning a part of a patient to be imaged denoted as the "structure of interest" under an X-ray tube, exposing the structure of interest to an X-ray beam, and recording the X-ray image on an image receptor. The receptor in most instances is a radiographic film disposed in contact with an intensifying screen. The intensifying screen absorbs x-ray radiation and radiates light in proportion to the radiation absorbed. Light emitted by the intensifying screen exposes the film. In an angiograph, the contrast agent causes highlights on the developed film of that portion of the circulatory system through which the contrast agent is flowing or highlights that organ or group of organs into Which the contrast agent has been ingested.

The problem with such previous angiographic techniques is the reliance on the administration of exogenous tracers, and such techniques may require arterial blood sampling for quantitation.

In recent years, there has been suggested the use of magnetic resonance imaging (MRI) techniques to produce angiographic like images. Such applications of MRI have been referred to as magnetic resonance angiography (MRA). MRA has the potential to provide detailed angiographic images of the human body. Additionally, MRA is non-invasive, with flow induced contrast substituting for iodinated contrast media. In order to appreciate MRA, a general summary of magnetic resonance techniques is appropriate.

Magnetic resonance (MR) is defined as the enhanced absorption of energy occurring when the nuclei of atoms or molecules within an external magnetic field are exposed to radio frequency (RF) energy at a specific frequency, called the Larmor or resonance frequency. Drs. Bloch and Purcell each received the Noble Prize for investigating and describing in 1946 the phenomenon of MR in solids and liquids. The characteristics of the MR signal arising from a given nucleus were found to depend on a specific molecular environment of that nucleus and such signal dependence proved ideal for qualitative and quantitative chemical analysis. Moreover, the radio frequencies involved in MR are non-ionizing and can penetrate the human body.

Although MR suggested enormous clinical potential for in vivo studies, the potential of the method was limited by its inability to provide spatial localization of the MR signal. Lauterbur resolved the localization problem through the use of magnetic field gradients. Since 1977, various MR techniques have been developed for the generation of two and three dimensional data of a human subject.

The production of an MR image can be generally summarized by the following steps. Randomly oriented nuclei are aligned by a powerful uniform magnetic field. This alignment of magnetization is disrupted by properly tuned RF pulses. These pulses disrupt or perturb the nuclei alignment. As the nuclei recover their alignment, they undergo relaxation processes and they precess producing radio signals proportional to the magnitude of their initial alignment. Contrast between nuclei develops as a result of the different relaxation rates at which each nuclei realigns with the magnetic field. The positions of the nuclei are localized by the application of spatially dependent magnetic fields called gradients. The radio signals produced by the processing nuclei are measured or "read out" after a predetermined time has elapsed from the initial RF excitation. The acquired signals are processed by means of the Fourier Transform into MR image data. See R. R. Edelman et al., Clinical Magnetic Resonance Imaging, W. B. Saunders (USA) (1990)(hereafter CMRI), incorporated herein by reference.

There are two important requirements for MRA which distinguish it from other MRI applications. First, high resolution is necessary in MRA in order to detail fine vascular anatomy. Second, high contrast is required in order to separate regions of flow from regions of stationary tissue.

The raw MR image data set, often referred to as "K space" is commonly parameterized by a quantity "K", which has dimensions of "cycles/centimeter", and which is related to the spatial parameter measured in "centimeters" through the Fourier Transform. The modern conceptualization of the MR imaging experiment is that the object to be imaged is directly sampled in its "K space" representation. See B. Twieg, The K-Space Trajectory Formulation Of The NMR Imaging Process With Applications In Analysis And Synthesis Of Imaging Methods, Medical Physics, Vol. 5, pp. 140–51 (1983). All characteristics of the digital sampling of K-space determine the sampling issues in image space. For example, the effective resolutions in the image-space and K-space are identical, as are the dimension of the acquisition, 2DFT versus 3DFT. On standard clinical imagers, 3DFT acquisitions offers higher spatial resolution in the slice direction than 2DFT imaging. Because resolution is essential to good quality MR images, 3DFT techniques in general enjoy an advantage over 2DFT methods for MRA.

Although conventional MR images will occasionally demonstrate striking contrast between blood vessels and background, producing an angiograph like image, in general, MR images obtained by standard two-dimensional Fourier transform (2DFT) methods are not well suited for angiography. MRA is a family of methods in which MR data is collected and computer processed in order to produce images resembling conventional x-ray angiograms. All methods require some way to generate contrast between flowing blood and stationary tissue. Prior MRA methods can be broadly divided into "white blood" and "black blood" techniques.

In "white blood" methods, signal from flowing blood is optimized while signal from stationary blood is suppressed. In "black blood" methods, signal from flowing blood is suppressed while signal from stationary blood is optimized. In other words, flowing blood is made to appear dark or black in black blood images and bright or white in white blood images. For a more complete discussion of MRA, see Listerud, J., First Principles of Magnetic Resonance Angiography, Magnetic Resonance Quarterly, Vol. 7, No. 2, pp. 136-170 (1991)(Listerud), incorporated herein by reference.

In standard MRI, two types of tuned RF signals have been suggested for perturbing nuclei, namely spin echo sequences and gradient echo sequences. Generally, a spin echo sequence is a pulse signal wherein an initial 90° pulse is transmitted followed at a prescribed time by a 180° pulse. The 90° pulse excites the protons producing an initial free induction decay (FID) signal. It will be understood that the FID signal is not directly used for imaging, but rather, an echo of the FID signal is used. The 180° pulse refocuses the transverse magnetization so that dephasing effects are cancelled at the time of the echo. The time period between 90° pulses is referred to as the repetition time (TR). A gradient echo sequence is a pulse sequence having an initial pulse, which is not necessarily 90° and is referred to as an alpha pulse to denote its variability. The echo is formed by a gradient manipulation and not by a 180° pulse. Consequently, the TR interval can be reduced significantly preserving good signal to noise.

Edelman reports that the generation of black blood angiographs using a combination of pre-saturation pulses, gradient echo pulses and so-called spoiler pulses gave very low contrast. RR Edelman, et al., Extracranial carotid arteries: Evaluation with "Black Blood" Angiography, Radiology, Vol. 177, pp. 45-50 (1990). One of the previous advantages of using gradient echo pulse sequences in MRA is the reduction in time required to generate a complete image, as compared to a spin echo sequence, especially when acquiring a three dimensional (3D) Fourier transform data set. For example, CMRI reports that TR for spin echo sequences cannot be reduced much below 200 msec. Imaging time for 3D Fourier transform spin echo data was regarded as prohibitive, on the order of one hour or more. However, spin echo sequences produce greater "Black Blood" contrast than gradient echo sequences.

Consequently, a need exists for methods which result in the production of non-invasively obtained angiographs by using MRI techniques, i.e. without the need for the administration of exogenous agents, and which provides greater resolution and shorter imaging times than those MRA methods presently employed.

The present invention resolves the above problems through the use of so-called fast spin echo sequences. Through the use of this technique, not only is greater Black Blood resolution possible, but also, the need for presaturation pulses and spoiler pulses is reduced. Although fast spin echo sequences have been known in the past, their use has been largely ignored because image quality has been inadequate. However, this sequence has been reported as being implemented recently on a 1.5T SIGNA, GE Medical Systems. The generation of black blood angiographs using fast spin echo sequences has not been reported and such use and adaptation forms the basis of the novel nature of the invention.

SUMMARY OF THE INVENTION

The advantages of the invention are achieved in a methods for producing an angiograph of a body portion. Such methods include the steps of subjecting the body portion to electromagnetic energy, i.e. positioning the body portion in a magnetic field, so as to cause a response related to the magnetization of the body portion, i.e. alignment of nuclei in relation to the direction of the magnetic field. Fast spin echo magnetic resonance measurements are performed on a three dimensional section of the body portion to generate three dimensional intensity information. The three dimensional intensity information is thereafter processed, preferably using ray tracing techniques, to construct an angiograph. In a preferred embodiment magnetic resonance data is produced by generating a slice gradient, generating a "z axis" slab selective 90° pulse, generating a z axis slab selective 180° pulse, generating a first phase encoding gradient pulse for a particular $K_y$ coordinate, generating a second phase encoding gradient pulse for a particular $K_z$ coordinate, and generating an x frequency encoding gradient and reading echo signal data from the body portion resulting from the 180° pulse. The method is repeated from the step of generating the 180° pulse, wherein the particular $K_z$ coordinate is incremented for each repetition. The method is thereafter repeated from the step of generating a 90° pulse, wherein the particular $K_y$ component is incremented after the $K_z$ coordinate has been incremented a prescribed number of times. In one embodiment of the invention, it is preferred to generate a sequence of sixteen 180° pulses. In another especially preferred embodiment, it is preferred to excite and detect from other slabs for various repetitions of the $K_z$ coordinate, before incrementing the $K_y$ coordinate. Echo signal data read from the body portion is processed to produce an image. It is preferred for such data processing to include transforming the data by a Fourier transform and performing ray tracing on the transformed data.

BRIEF DESCRIPTION OF THE DRAWINGS

The present invention will be better understood, and its numerous objects and advantages will become apparent to those skilled in the art by reference to the following detailed description of the invention when taken in conjunction with the following drawings, in which.

DETAILED DESCRIPTION OF THE PREFERRED EMBODIMENT

The methods of the present invention produce angiographic like images, particularly black blood images, using MRI equipment and techniques. Consequently, before describing such new and novel methods, a general description of the equipment preferred for practicing the invention will be described.

Figure 1:
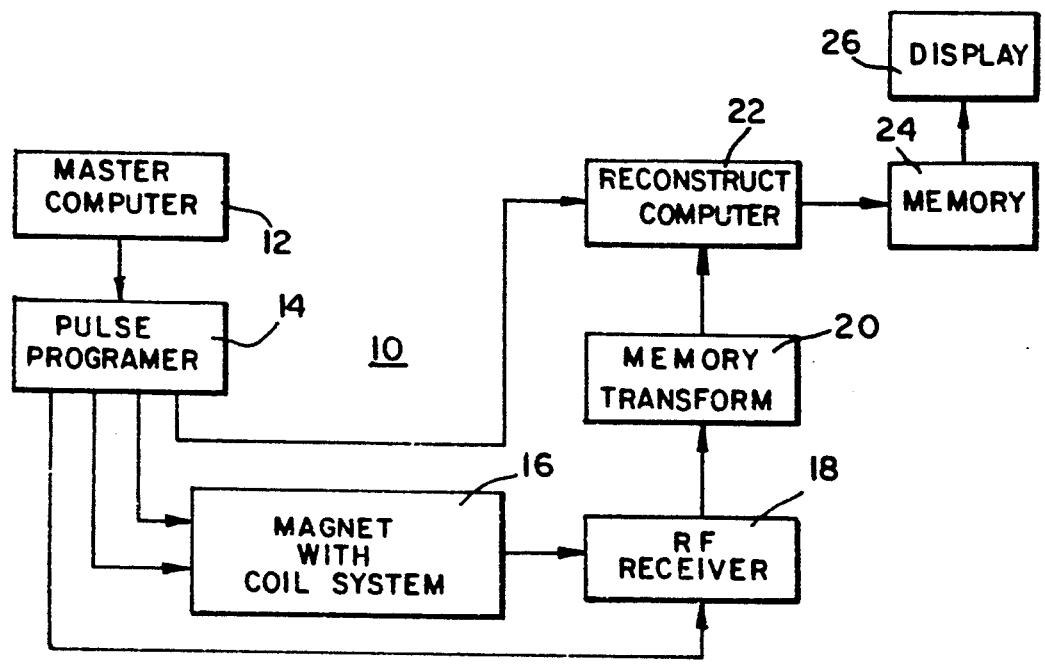
FIG. 1 is a block diagram of an MRA apparatus for use with the present invention.

Referring to FIG. 1, the pertinent portions of an MRI device 10 is depicted in block form. In the preferred embodiment, device 10 is an 1.5 T SIGNA device, manufactured and sold by General Electric Medical Systems. It will be recognized that device 10 includes more components than those depicted, however, for purposes of explaining the operation of the present invention, the depiction is sufficient. A master computer 12 controls a pulse programmer 14. It will be appreciated that master computer 12 is used to program pulse programmer 14 in order to generate desired pulse sequences and to control acquisition of magnetic resonance data.

Magnet and coil system 16 generates the primary magnetic field, various localization and encoding gradients and all pulse sequences in response to signals generated by pulse programmer 14. RF receiver 18 receives the radio signals transmitted by processing nuclei within magnet and coil system 16 and such signals are stored in memory/transform processor 20 in response to signals generated by pulse programmer 14. This latter hardware feature of the preferred embodiment enhances operation of the invention.

Processor 20 performs a Fourier transform operation on the data stored in the memory and provides the transformed data to reconstruct computer 22. As will be described herein, reconstruct computer 22 interrogates the transformed data and generates a series of projections. The projections are stored in memory 24, which in the preferred embodiment is a hard disk drive, and such stored projections are displayed on display 26. It is preferred for display 26 to include a video monitor.

Figure 2:
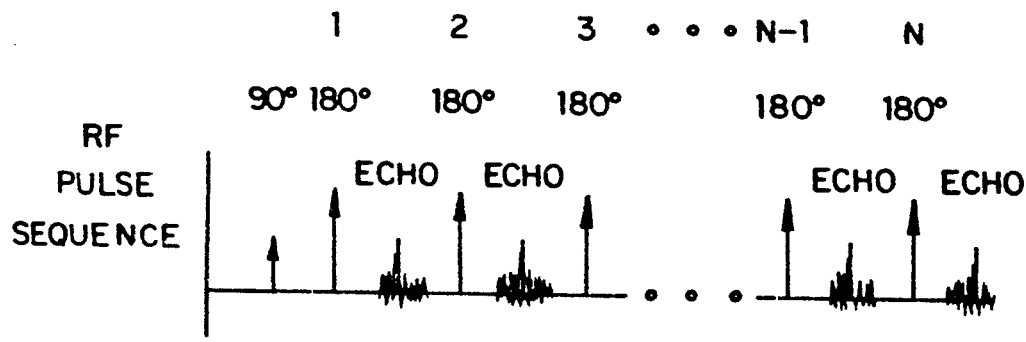
FIG. 2 is a graph depicting a fast spin echo sequence for use with the present invention.

In generating black blood angiographic images, the present invention utilizes a fast spin echo sequence implemented in a three dimensional Fourier transform process. The preferred fast spin echo sequence is depicted in FIG. 2. As shown in FIG. 2, a 90° pulse and a following 180° pulse at time TE/2, where TE will be understood to represent the echo time, are generated similar to typical spin echo sequences. However, after acquisition of the echo at time TE, a further 180° pulse is generated. Additional 180° pulses are generated, so that the time between each echo is substantially constant. In the preferred embodiment, the time between echoes equals 20 msec and N equals 16. Accordingly, the entire fast spin echo sequence depicted in FIG. 2 will last for approximately 320 msec. The fast spin echo sequence described will be generated in device 10 by pulse programmer 14.

Consider now the particulars of the methods of the present invention. In its most general form the invention is a method for producing an angiograph of a body portion (not shown) and broadly includes the steps of subjecting the body portion to electromagnetic energy so as to cause a response related to the magnetization of the body portion. Those familiar with this art, will recognize this step as the application of a primary magnetic field to the body portion for the purpose of aligning nuclei with the magnetic field. Next, fast spin echo magnetic resonance measurements are performed on a three dimensional section of the body portion to generate three dimensional intensity information. The specifics of such measurements are described below. Finally, the three dimensional intensity information is processed to produce an angiograph. Such processing is also described below.

Consider now the details of performing fast spin echo magnetic resonance measurements on a three dimensional section. It is assumed that the body portion has been subjected to a primary magnetic field, generated by magnet 16. The measurements will be described as numbered steps for ease in describing "loops" within the method. It is noted that magnetic resonance data generated by the invention is generated in K space, wherein K space defines x, y and z coordinates. It will be understood that such K space is related to the three dimensional volume formed by the body portion by a Fourier transform. In other words, the processing of data in K space coordinates by processor 20 conducting Fourier transforms, transforms the magnetic resonance or spin echo data into data which is spatially located in relation to the x, y, z coordinate system of the body portion. In particular, $K_x$ may in fact be parallel to physical z: the assignment of K space axes to physical axes is arbitrary.

The first step having been completed (application of a primary magnetic field), the second step is for pulse programmer 14 to generate a slice gradient which is applied to the body portion by member 16. Third, pulse programmer 14 generates a z axis slab selective 90° pulse, which pulse is transmitted by magnet and coil system 16. Fourth, after waiting a prescribed time τ, pulse programmer 14 generates a z axis slab selective 180° pulse which is also applied by coil system 16. Fifth, pulse programmer 14 generates a first phase encoding gradient for a particular $K_y$ coordinate, which gradient is applied by member 16. Sixth, pulse programmer 14 generates a second phase encoding gradient for a particular $K_z$ coordinate, which gradient is also applied by member 16. Seventh, pulse programmer 14, generates an x frequency encoding gradient and echo signal data from said body portion is "read out" or received by RF receiver 18. Pulse programmer 14 controls when signals received by RF receiver 18 are transmitted to processor 20. Eighth, steps 4, 5, 6 and 7, are repeated, wherein each repetition of step 6 results in the generation of a modified second phase encoding gradient representative of the particular $K_z$ coordinate incremented through K space while $K_y$ is constant. Ninth, steps 3, 4, 5, 6, 7 and 8 are repeated after an interval TR - the repetition time, wherein each completion of step 8 results in the generation of a modified first phase encoding gradient representative of the particular $K_y$ coordinate incremented through K space. In this fashion, the fast spin echo sequence is utilized in the invention to generate echo signal data throughout K space.

In the preferred embodiment of the invention, step 8 is repeated sixteen times, i.e. N equals sixteen, and the repetition of step 4 occurs at 20 msec intervals. It is noted that N is also referred to as the echo train length (ETL). It is also noted that while N has been made equal to 16, this number is not meant to imply any limiting significance. The number 16 is chosen due to the hardware and software limitations of MR device 10. As more flexible hardware and software become available, it may be desirable to repeat step 8 more than sixteen times.

Thus, the overall time for the fast spin echo sequence is 320 msec. It is also preferred to make measurements of multiple slabs within the same overall repetition time (TR). If TR is chosen to be 1000 msec, three fast spin echo sequences are possible (3×320=960 msec). In such a method it is preferred to repeat the fast spin echo sequence three times so that a particular sequence acquires data from a unique slab and the data is assigned to a unique K space. The three fast spin echo sequences will acquire data from the three different slabs and assign the data to three different K spaces. It is noted that during each of the three fast spin echo sequences, it is preferred that the $K_y$ coordinate not be incremented.

In order for data from multiple slabs to be gathered, as in the previous paragraph, it will be necessary to repeat the fast spin echo sequence while generating modified z axis slab selective pulses, wherein the slab selection is representative of the incrementation of the x coordinate through K space. It may also be desirable to generate the slab selective pulses, numbering the slabs sequentially, so that data is first acquired from all even designated slabs and thereafter from all odd designated slabs, wherein each slab is of a uniform thickness.

It is also preferred for pulse programmer 14 to generate phase re-winding gradients after each step 7 for dephasing the effects of the first and second phase encoding gradients. Such phase re-winding or dephasing gradients are known in the art and need not be further described.

As indicated above, MRA involves the collection of data which is thereafter computer processed in order to produce images resembling conventional x-ray angiograms. Such processing is carried out using reconstruct computer 22. Such processing will include transforming the K space data by a Fourier transform and performing 3D depth cued lateral projections on the transformed data. It will be appreciated that several spatial assignment methods, such as maximum intensity pixel (MIP) ray tracing, are known and can be used to support 3D depth cuing feature extraction. See Listerud for a more detailed description of some of these processing techniques.

In the development of the methods of the present invention, an experiment was conducted. It was desired to compare the black blood angiographs obtainable with the present invention to images obtainable using two dimensional Fourier transform (2DFT) Time-of-Flight Imaging. A mosaic pass through K space was made using the methods of the invention. Up to 16 lines of K space were encoded per TR. Sagittal images were obtained using 2 excitations, TR of 1000–1500 msec, effective TE of 23 msec. Multiple slab acquisition encompassed both left and right carotid arteries. Axial 2DFT "bright blood" images were obtained using sequential slice spoiled GRASS imaging with tracking saturation, wherein TR equaled 45 msec., TE equaled 8 msec, the flip angle equaled 60° and contiguous 1.5 mm slices were made. Projection images were obtained using MIP techniques and traced ray by array processor (TRAP—see Listerud) techniques. Images were acquired on a 1.5 T SIGNA system.

Acquisition times were 8:38 to 12:45. Projection images were generated using the traced ray array processor technique. In normal volunteers and in patients, the patent lumen, even in regions of proven tight stenosis, was clearly demonstrated. The normal zone of stasis in the carotid bulb, seen as the absence of flow on "bright blood" techniques, generally appeared as low intensity (i.e. flow) on images obtained using the fast spin echo technique, but heterogeneity was sometimes noted. Atherosclerotic plaque was clearly seen as high intensity on the acquired images.

While the invention has been described and illustrated with reference to specific embodiments, those skilled in the art will recognize that modification and variations may be made without departing from the principles of the invention as described herein above and set forth in the following claims.

What is claimed is:

1. A method for producing an angiograph of a body portion, wherein a fluid passes into said body portion, said method comprising the steps of:

subjecting said body portion to electromagnetic energy so as to cause a response related to the magnetization of said body portion;

performing fast spin echo magnetic resonance measurements on a three dimensional section of said body portion to generate K space oriented intensity information; and processing said K space intensity information to produce a black blood angiograph.

2. A method for generating magnetic resonance data of a body portion, said magnetic resonance data being generated in K space, wherein said K space defines z axis, $K_y$ and $K_z$ coordinates, said method comprising the steps of:

1) subjecting said body portion to electromagnetic energy so as to cause a response related to the magnetization of said body portion;
   2) generating a slice gradient;
   3) generating a z axis slab selective 90° pulse;
   4) generating a z axis slab selective 180° pulse;
   5) generating a first phase encoding gradient pulse for a particular $K_y$ coordinate;
   6) generating a second phase encoding gradient pulse for a particular $K_z$ coordinate;
   7) generating an x frequency encoding gradient and reading echo signal data from said body portion resulting from said 180° pulse;
   8) repeating steps 4, 5, 6 and 7, wherein each repetition of step 6 results in the generation of a modified second phase encoding gradient pulse representative of the particular $K_z$ coordinate incremented through K space; and
   9) repeating steps 3, 4, 5, 6, 7 and 8, wherein each completion of step 8 results in the generation of a modified first phase encoding gradient pulse representative of the particular $K_y$ coordinate incremented through K space.

3. The method of claim 2, wherein step 8 is repeated sixteen times.

4. The method of claim 3, wherein the repetition of step 4 occurs at 20 msec intervals.

5. The method of claim 4, further comprising a step of repeating three times the step of repeating step 8 sixteen times, wherein the slab selective pulses are modified so that data is acquired from three different slabs.

6. The method of claim 2, wherein step 9 is repeated, further comprising the step of generating modified slab selective pulses, wherein the slab selective pulses are modified for each repetition of step 9 so that the slab selection is representative of the incrementation of the z axis through K space.

7. The method of claim 2, further comprising a step of generating phase re-winding gradients after each step 7 for dephasing the effects of said first and second phase encoding gradients.

8. The method of claim 2, wherein TR equals 1000 ms.

9. The method of claim 2, further comprising a step of processing the echo signal data read from said body portion to produce an image.

10. The method of claim 9, wherein said step of processing said echo signal data comprises steps of transforming the data by a Fourier transform and performing feature extraction on the transformed data.

* * * * *

UNITED STATES PATENT AND TRADEMARK OFFICE
CERTIFICATE OF CORRECTION

PATENT NO. : 5,271,399

DATED : December 21, 1993

INVENTOR(S) : John Listerud and Scott Atlas

It is certified that error appears in the above-identified patent and that said Letters Patent is hereby corrected as shown below:

Column 1, lines 34-36  "or highlights that organ or group of organs into Which the contrast has been ingested" should be typed as and  highlights that organ or group of organs through which the contrast agent is passing"

Signed and Sealed this

Fourteenth Day of June, 1994

*Attest:*

BRUCE LEHMAN

*Attesting Officer*  *Commissioner of Patents and Trademarks*